(12) United States Patent
Holmqvist (10) Patent No.: US 8,926,568 B2
(45) Date of Patent: Jan. 6, 2015

(54) MEDICAMENT DELIVERY DEVICE COMPRISING A MANUAL ACTIVATION MEMBER WITH IMPROVED GRIPPING AND ACTIVATION ABILITIES

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 169 days.

(21) Appl. No.: 13/698,731

(22) PCT Filed: May 9, 2011

(86) PCT No.: PCT/SE2011/050577
§ 371 (c)(1),
(2), (4) Date: Dec. 1, 2012

(87) PCT Pub. No.: WO2011/145998
PCT Pub. Date: Nov. 24, 2011

(65) Prior Publication Data
US 2013/0211336 A1 Aug. 15, 2013

Related U.S. Application Data

(60) Provisional application No. 61/346,682, filed on May 20, 2010.

(30) Foreign Application Priority Data

May 20, 2010 (SE) ........................ 1050501

(51) Int. Cl.
*A61M 5/00* (2006.01)
*A61M 5/315* (2006.01)
*A61M 5/24* (2006.01)
*A61M 5/31* (2006.01)

(52) U.S. Cl.
CPC .............. *A61M 5/3155* (2013.01); *A61M 5/24* (2013.01); *A61M 5/31511* (2013.01); *A61M 5/31553* (2013.01); *A61M 5/31558* (2013.01); *A61M 5/31575* (2013.01); *A61M 5/31576* (2013.01); *A61M 5/31561* (2013.01); *A61M 5/31593* (2013.01); *A61M 2005/3104* (2013.01); *A61M 2005/3152* (2013.01); *A61M 2205/586* (2013.01)
USPC .......................... 604/207; 604/224; 604/187

(58) Field of Classification Search
USPC ................. 604/151, 181, 187, 207–211, 224
See application file for complete search history.

(56) References Cited

U.S. PATENT DOCUMENTS 5,645,534 A 7/1997 Chanoch
6,582,404 B1 * 6/2003 Klitgaard et al. ............. 604/181
(Continued)

FOREIGN PATENT DOCUMENTS

WO 2008/101829 A1 8/2008
WO WO 2009/016637 * 2/2009

OTHER PUBLICATIONS

Swedish Patent Office, Int'l Search Report in PCT/SE2011/050577, Aug. 31, 2011.
Swedish Patent Office, Written Opinion in PCT/SE2011/050577, Aug. 12, 2012.

*Primary Examiner* — Matthew F Desanto
(74) *Attorney, Agent, or Firm* — Piedmont Intellectual Property (57) ABSTRACT

A medicament delivery device includes a housing for a medicament container assembly; a drive member interactively connected to the assembly for expelling a dose of medicament; a dose actuation assembly operably connected to the drive member; and an actuation member interactively connected to the housing and the dose actuation assembly by a gear assembly. The actuation member is movable generally perpendicularly to a longitudinal axis of the device from an initial position, in which the actuation member is positioned within the housing, to a dose-set position, in which a portion of the actuation member protrudes a distance proportional to the set dose from the longitudinal surface of the housing when the dose actuation assembly. The actuation member is manually operated in a direction generally perpendicular to the longitudinal axis of the device from the dose-set position to the initial position for driving the dose actuation assembly and drive member.

19 Claims, 10 Drawing Sheets

(56) References Cited

U.S. PATENT DOCUMENTS

| | | | |
|---|---|---|---|
| 6,599,272 | B1 | 7/2003 | Hjertman et al. |
| 2002/0007154 | A1 | 1/2002 | Hansen et al. |
| 2004/0247453 | A1 | 12/2004 | Denolly |
| 2005/0090781 | A1* | 4/2005 | Baba et al. .................... 604/209 |
| 2007/0060894 | A1* | 3/2007 | Dai et al. ...................... 604/207 |

* cited by examiner

Fig. 7

MEDICAMENT DELIVERY DEVICE COMPRISING A MANUAL ACTIVATION MEMBER WITH IMPROVED GRIPPING AND ACTIVATION ABILITIES

TECHNICAL AREA

The present invention relates to a medicament delivery device having a dose setting function connected to a manual activation member with improved gripping and actuation abilities for users.

BACKGROUND OF INVENTION

Handheld medicament delivery devices are well known products and are frequently used for self-medication by patients or users as part of treatment in a large variety of disorders and conditions, for instance insulin injectors used by diabetes patients. From a user's perspective it is desired that the medicament delivery device is both intuitive and easy to handle, particularly in case the patient suffers from reduced gripping strength in which case e.g. a pen-shaped injector may not be very easy to operate since it is sometimes hard to grip and at the same time perform penetration and injection, especially if the device is also manually operated.

WO2006007590A2 and WO2008107813A1 disclose medicament delivery devices where an improved gripping for manually activating a delivery by squeezing a pivot lever, however, each time the lever is squeezed a pre-determined dose of medicament is delivered. A solution where a dose assembly is connected to a squeezing pivot lever is known in WO2004035112A2. However, for manually actuated medicament delivery devices it is neither necessary nor desirable to use a pivot lever since they would be difficult to grip and activate. When the pivot lever is in an activated position, an angle of least 30 degrees between the pivot lever and the longitudinal axis of the device is formed. Such an activated position of the pivot lever means that the individual who is activating the device has to exert at first a force with his/her little finger. This is not so convenient for individuals having dexterity problems.

Also from a manufacturer's point of view it is of course advantageous if the injector is easy to produce at a cost-efficient price and at the same time keep a high quality standard. For various reasons many injectors are disposable devices which is another reason why it is advantageous to be able to keep the prices down so that buyers will not refuse the product because it is too expensive.

BRIEF DESCRIPTION OF INVENTION

A first object of the present invention is to provide a manually operated medicament delivery device that is reliable and easy to use when handling and activating, and that provides a secure grip for different users having various gripping capacities. It is also an object of the present invention to provide a disposable medicament delivery device which is easy to produce and may be manufactured to low production cost.

The objects of the present invention are achieved, according to a main aspect of the invention, by a medicament delivery device comprising a housing having opposite distal and proximal ends, and adapted to store a medicament container assembly to which a delivery member may be attached; a drive member interactively connected to said medicament container assembly for expelling a dose of medicament; a dose actuation assembly operably connected to said drive member; and an actuation member interactively connected to said housing and as well as to said dose actuation assembly by a gear assembly; wherein the actuation member comprises gear racks extending in a direction generally perpendicular to the longitudinal axis of the device and being arranged in engagement with the gear assembly whereby said actuation member is arranged to be movable in a direction generally perpendicular to a longitudinal axis of the device from an initial position in which the actuation member is positioned within the housing to a dose-set position in which a portion of the actuation member protrudes a certain distance, proportional to the set dose, from the longitudinal surface of the housing when the dose actuation assembly is manually operated for setting a dose and wherein the actuation member is arranged to be manually operated in a direction generally perpendicular to the longitudinal axis of the device from the dose-set position to the initial position for driving the dose actuation assembly and thereby the drive member.

According to another aspect of the invention said gear assembly comprises first gear wheels and second gear wheels fixedly attached to said first gear wheels, wherein said first and second gear wheel are rotatably connected to the housing, and wherein said first gear wheels have a pitch circle diameter larger than the pitch circle diameter of said second gear wheels for providing a gear ratio.

According to yet another aspect of the invention, the dose actuation assembly comprises a tubular dose actuation member and a dose setting knob connected to each other.

According to a further aspect of the invention, said tubular dose actuation member and said drive member are interactively connected to each other by threads arranged on the outer surface of the drive member and on the inner surface of the tubular dose actuation member.

According to yet a further aspect of the invention, said tubular dose actuation member comprises a gear rack on its outer circumferential surface, and wherein said gear rack is arranged to interact with said second gear wheels.

According to another aspect of the invention, said gear racks of the actuation member extends in said generally perpendicular direction and are arranged in engagement with said first gear wheels, such that when said dose setting knob is rotated for setting a dose, the tubular dose actuation member is moved in the distal direction due to the threaded connection with the drive member, and the actuation member is moved out of said housing from the initial position to the dose-set position.

According to yet another aspect of the invention, the housing comprises a dose quantity window in which indicia are displayed, and which indicia correspond to certain dose quantities.

According to a further aspect of the invention, said indicia are arranged on a side surface of said actuation member.

According to yet a further aspect of the invention, said indicia is arranged on a circumferential surface of a drum, which drum is interactively connected to said first gear wheels through third and fourth gear wheels.

According to yet another aspect of the invention the third gear wheels are fixedly attached to the first gear wheels and wherein the fourth gear wheels are fixedly attached to the drum.

According to another aspect of the invention, the device further comprises guides arranged to act on longitudinally extending grooves arranged on the outer surface of said drive member for allowing a longitudinal movement but preventing rotation of said drive member.

According to yet another aspect of the invention, the device further comprises a one-way locking means arranged to interact with the drive member for allowing longitudinal movement of the drive member only in the proximal direction.

According to a further aspect of the invention, said device is an injector.

Thanks to the actuating member being arranged in a direction generally perpendicular to said longitudinal axis of the injection device a steady and ergonomic grip is permitted and a steady force for activating the device can be applied where even patients with weakened hand strength may readily activate the medicament delivery device performing penetration and injection.

The medicament delivery device according to the present invention presents a number of further advantages. There is a high degree of functionality which removes unnecessary components and actions for delivering a medicament leading to reduced production costs. A safe delivery system is provided in that the drive member for each dosage injection is positioned to be ready for the next delivery until the medicament container has been emptied.

By the term manually operated medicament delivery device, is herein meant a medicament delivery device adapted to deliver a medicament by means of a user manually pressing a push button or activation member as he/she presses the proximal end of the medicament delivery device against the delivery site.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site. Correspondingly, when the term "proximal part/end" is used, this refers to the part/end of the medicament delivery device, or the parts/ends of the members thereof, which under use of the medicament delivery device is located closest to the medicament delivery site.

The present invention relates to a medicament delivery device comprising a housing having opposite distal and proximal ends, and adapted to store a medicament container assembly to which a delivery member may be attached; a drive member interactively connected to said medicament container assembly for expelling a dose of medicament; a dose actuation assembly operably connected to said drive member; and an actuation member interactively connected to said housing as well as to said dose actuation assembly by a gear assembly; wherein the actuation member comprises gear racks extending in a direction generally perpendicular to the longitudinal axis of the device and being arranged in engagement with the gear assembly whereby said actuation member is arranged to be movable in a direction generally perpendicular to a longitudinal axis of the device from an initial position in which the actuation member is positioned within the housing to a dose-set position in which a portion of the actuation member protrudes a certain distance, proportional to the set dose, from the longitudinal surface of the housing when the dose actuation assembly is manually operated for setting a dose and wherein the actuation member is arranged to be manually operated in a direction generally perpendicular to the longitudinal axis of the device from the dose-set position to the initial position for driving the dose actuation assembly and thereby the drive member.

An exemplary embodiment of the invention, but not restricted to it, is shown in the FIGS. 1-7. The exemplary embodiment is a medicament delivery device and more particularly a manually operated injection device. The exemplary device comprises a generally elongated housing 10 having opposite distal 18 and proximal 24 ends, and adapted to store a medicament container assembly 12 to which a delivery member (e.g. an injection needle, a mouth piece, a nozzle or the like) may be attached, which container assembly 12 contains medicament to be expelled through said medicament delivery member. Further, a drive member 14, herein also referred to as "plunger rod", is arranged within the elongated housing 10 and is capable of acting on a movable stopper 16 (see FIG. 4) inside the container assembly 12 thereby being interactively connected to said medicament container assembly 12 for expelling a dose of medicament. A dose actuation assembly 22 is operably connected to said drive member 14. An actuation member 26 is interactively connected to said housing 10 as well as to said dose actuation assembly 22 by a gear assembly 32. The device further comprises a protective cap 52 releasably attached to the proximal end of the housing 10. The proximal end 24 of the housing 10 is arranged with a neck portion 56 arranged with engagement means as e.g. thread segments on its outer surface and the protective cap 52 is releasably attached to the neck portion 56 by appropriate engagement means.

Said dose actuation assembly comprises a tubular dose actuation member 20 and a dose setting knob 34 connected to each other. The tubular dose actuation member 20 and said drive member 14 are interactively connected to each other by threads arranged on the outer surface of the drive member 14 and on the inner surface of the tubular dose actuation member 20. Further, in the exemplary embodiment, the housing 10 comprises guides 46, FIG. 3, arranged to act on longitudinally extending grooves 48 arranged on the outer surface of said drive member 14, FIG. 5b, for allowing a longitudinal movement but preventing rotation of said drive member. Also the housing 10 comprises a one-way locking means 50, FIG. 3, arranged to interact with the drive member for allowing longitudinal movement of the drive member 14 only in the proximal direction. According to the exemplary embodiment said locking means 50 comprises a transversally positioned locking plate 58 located at the proximal end of the tubular dose actuation member 20 where the plunger rod 14 exits from said dose actuation member 20. Said plate 58 comprises a central hole arranged to receive said plunger rod 14 in such a way that the plunger rod 14 projects through said hole. The plate 58 is attached to the housing 10 of the device thereby being kept from moving in a longitudinal direction. As is seen for instance in FIG. 3 the locking means 50 is further provided with at least one protruding locking tooth 68, preferably a plurality or locking teeth, directed towards the centre of said hole. The locking teeth 68 are engaging the threads on the outer surface of the drive member 14 in such a way allowing for movement of the drive member 14 in a proximal direction but preventing movement thereof in a distal direction.

Figure 5A:
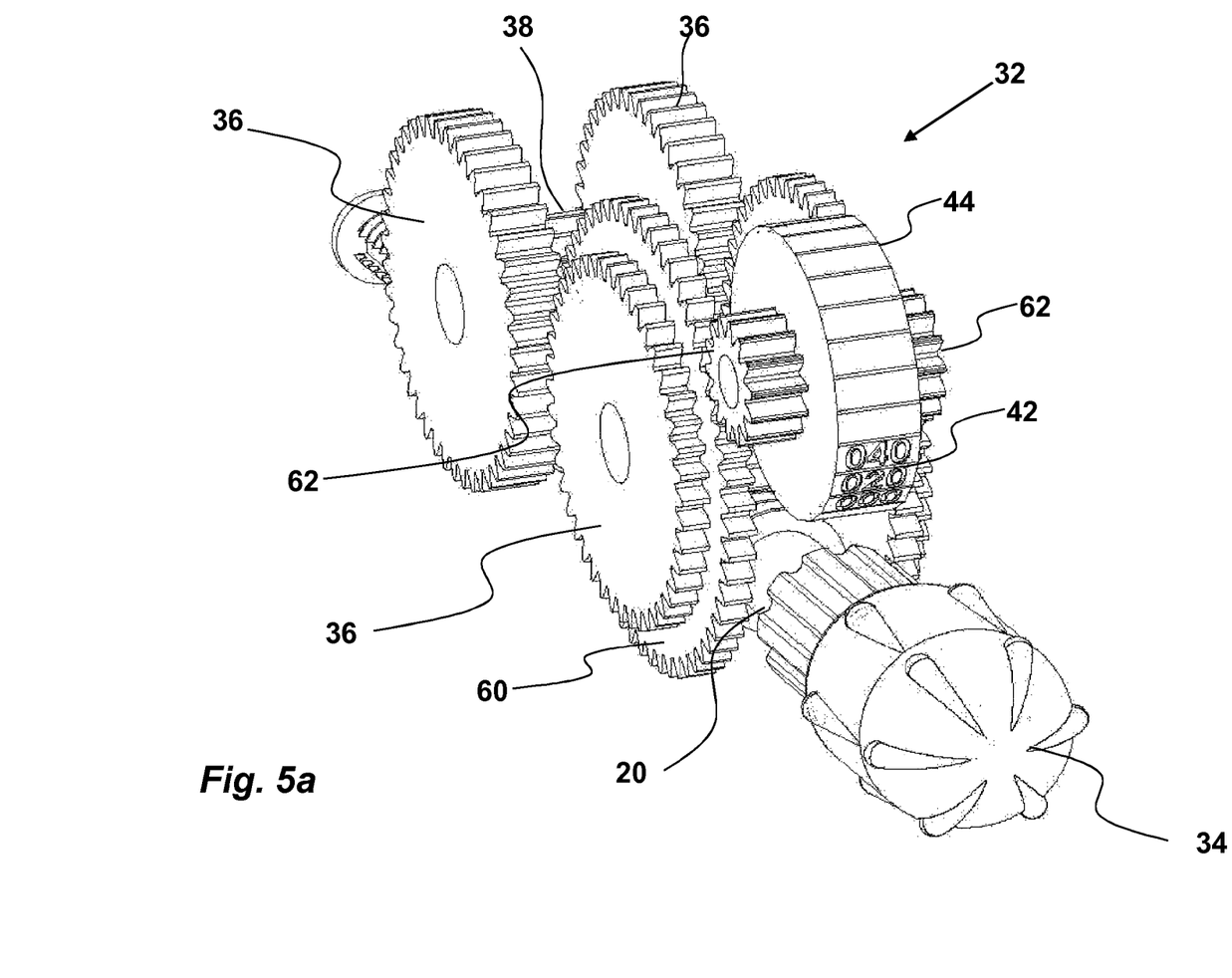
Figure 5B:
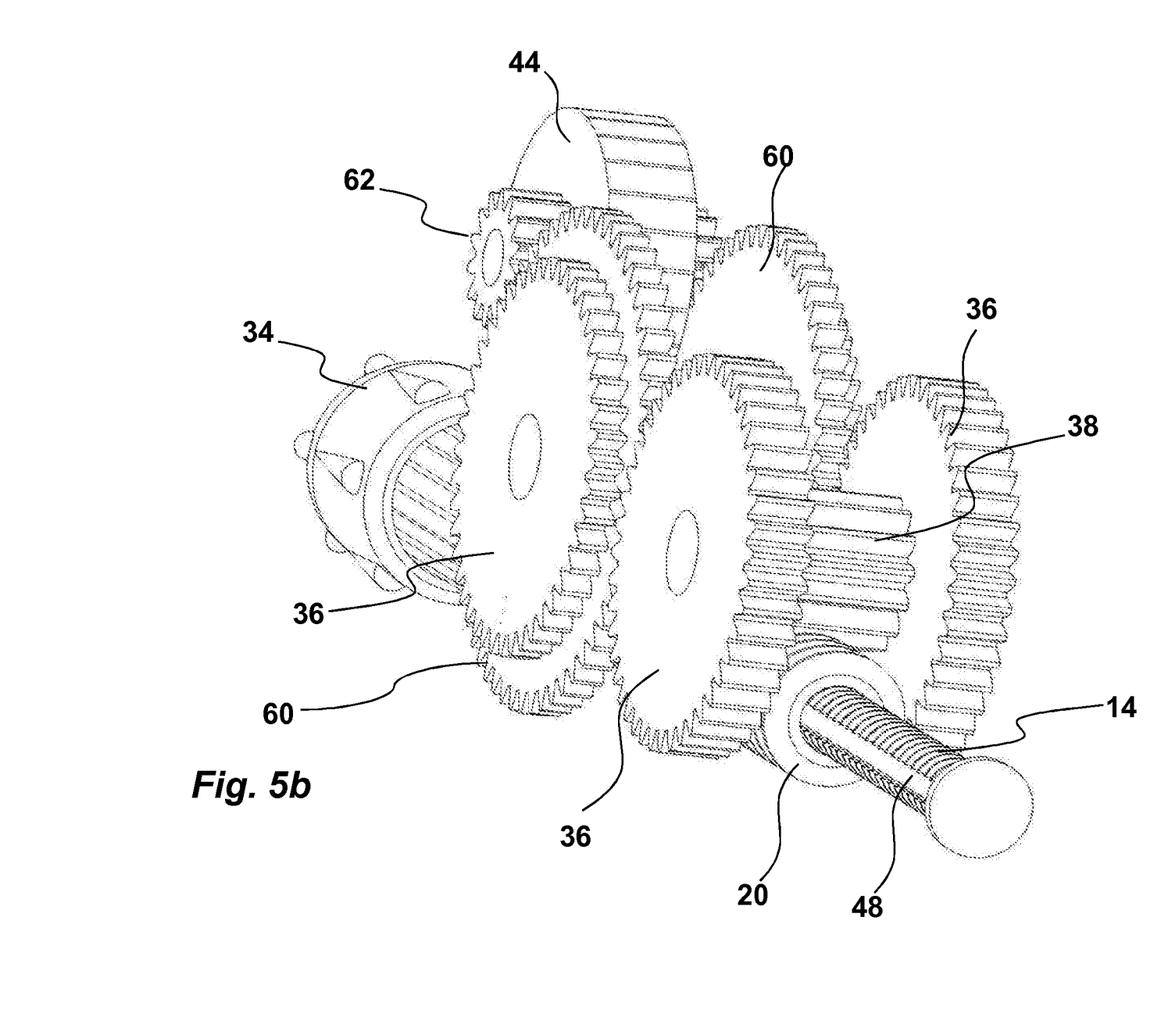
Figure 5C:
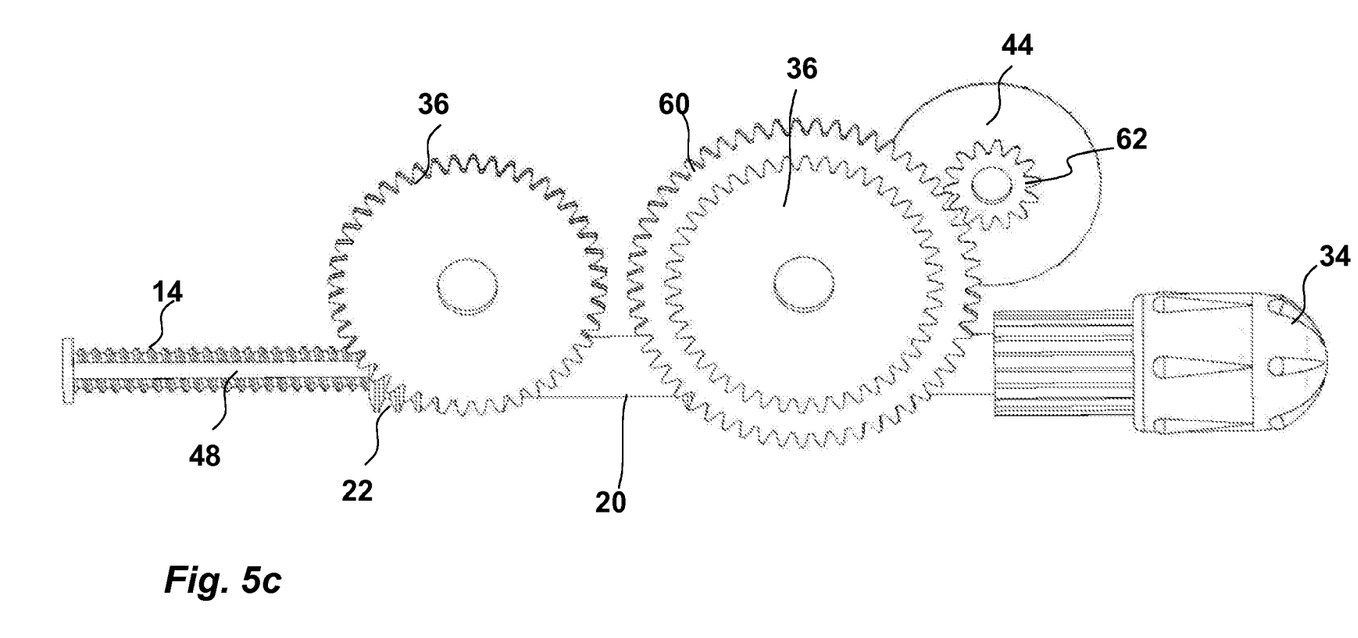
Figure 6:
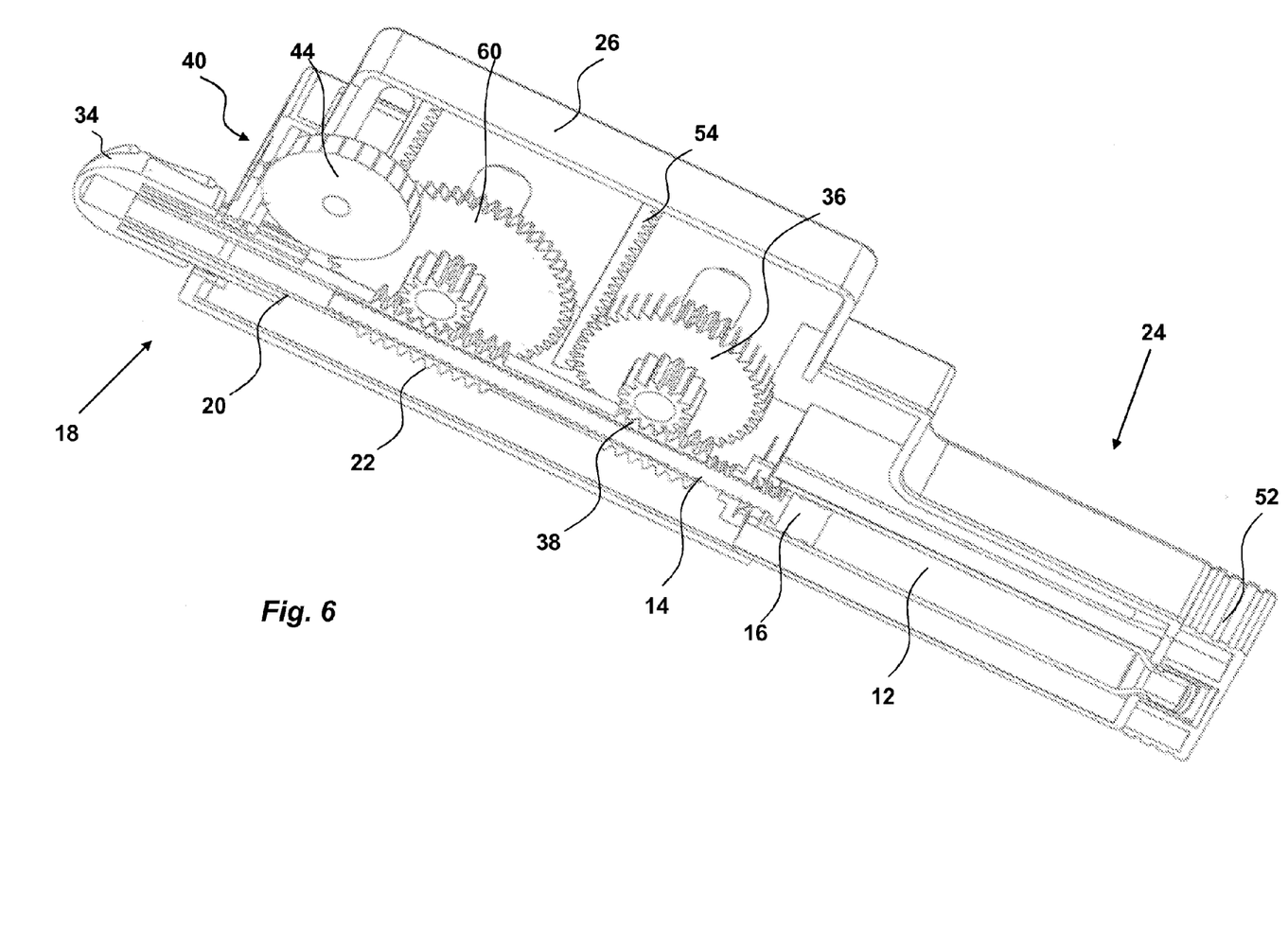
FIG. 6 is a perspective cross-sectional view of the device of FIG. 1.

Shown specifically in FIGS. 5a-5c are different views of said gear assembly 32 which comprises first gear wheels 36 and second gear wheels 38 fixedly attached to each other, wherein said first 36 and second 38 wheels are coaxial and are rotatably connected to the housing 10. Said first gear wheels 36 have a pitch circle diameter larger than the pitch circle diameter of said second gear wheels 38 for providing a gear ratio. Said tubular dose actuation member 20 comprises a gear rack 22 arranged on its outer circumferential surface, and said gear rack 22 is further arranged to interact with said second gear wheels 38. It should be noted that said gear rack 22 is not a helical thread but an axisymmetric development around the central axis of dose actuation member 20 of a series of rack gear profiles.

The actuation member 26 comprises gear racks 54 extending in said generally perpendicular direction and being arranged in engagement with said first gear wheels 36, such that when said dose setting knob 34 is rotated for setting a dose, the tubular dose actuation member 20 is moved towards the distal direction due to the threaded connection with the drive member 14, and the actuation member 26 is moved out of said housing 10 from the initial position to the dose-set position. The housing 10 comprises a dose quantity window 40 in which indicia 42 are displayed, and which indicia 42 correspond to certain dose quantities. Said indicia 42 may be arranged on the circumferential surface of a drum 44, which drum 44 is interactively connected to said gear assembly 32 via third 60 and fourth 62 gear wheels, wherein the third gear wheels are fixedly attached to the first gear wheels 36 and wherein the fourth gear wheels 62 are fixedly attached to the drum 44. Hereby rotational movement from the second gear wheels 38 is transmitted to third gear wheels 60 which in their turn engage the fourth 62 gear wheels. As seen for instance in FIG. 5a, the fourth gear wheels 62 are attached onto a drum 44 which displays, on its circumferential surface, said indicia 42. Thus rotational movement of the second gear wheels 38 will lead to rotation of said drum 44 and thereby to change of position of said indicia 42. It is to be understood that said indicia 42 may equally be arranged on a side surface of said actuation member 26.

Figure 1:
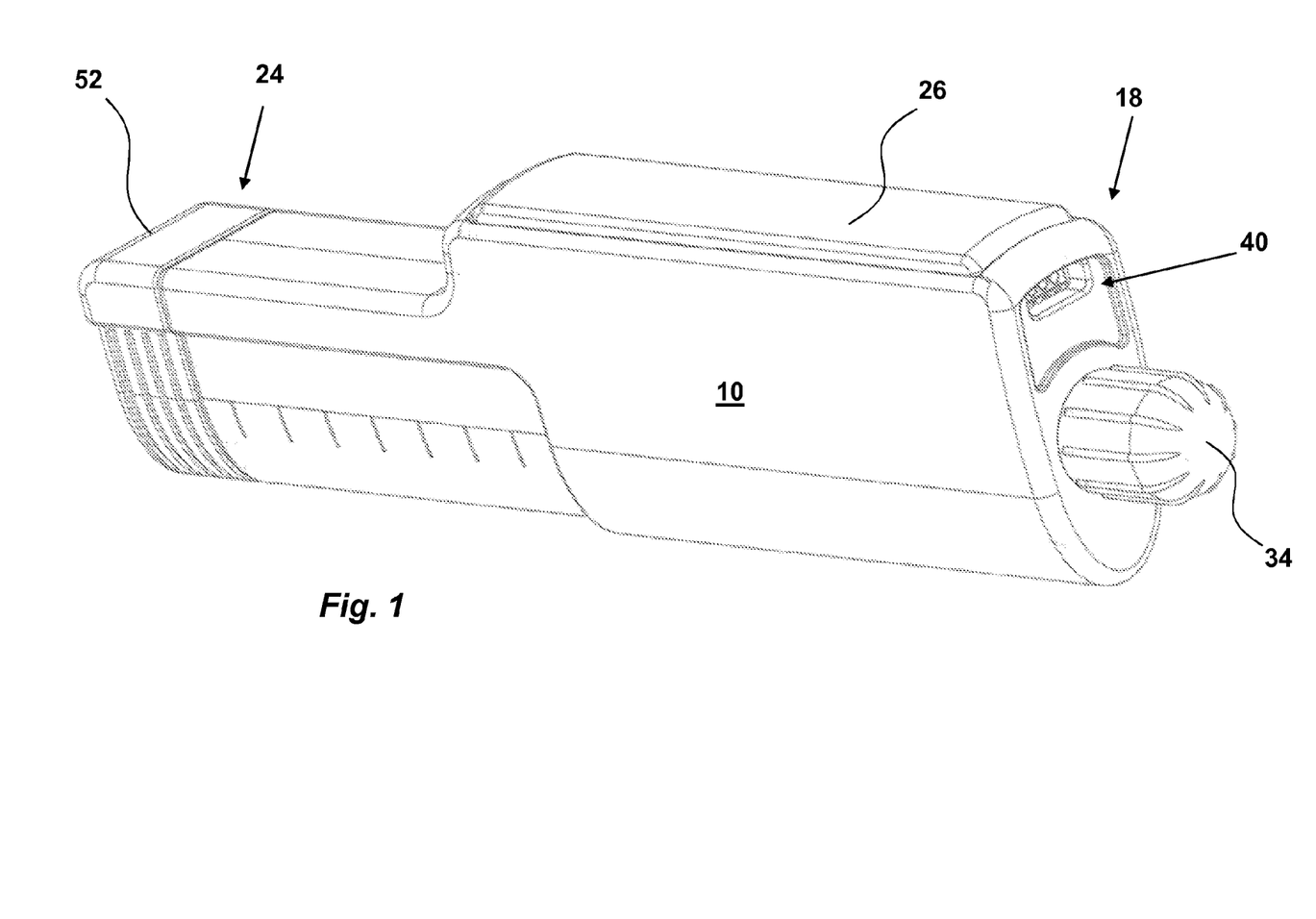
FIG. 1 is a perspective view of a medicament delivery device of the present invention in a rest position.
Figure 2:
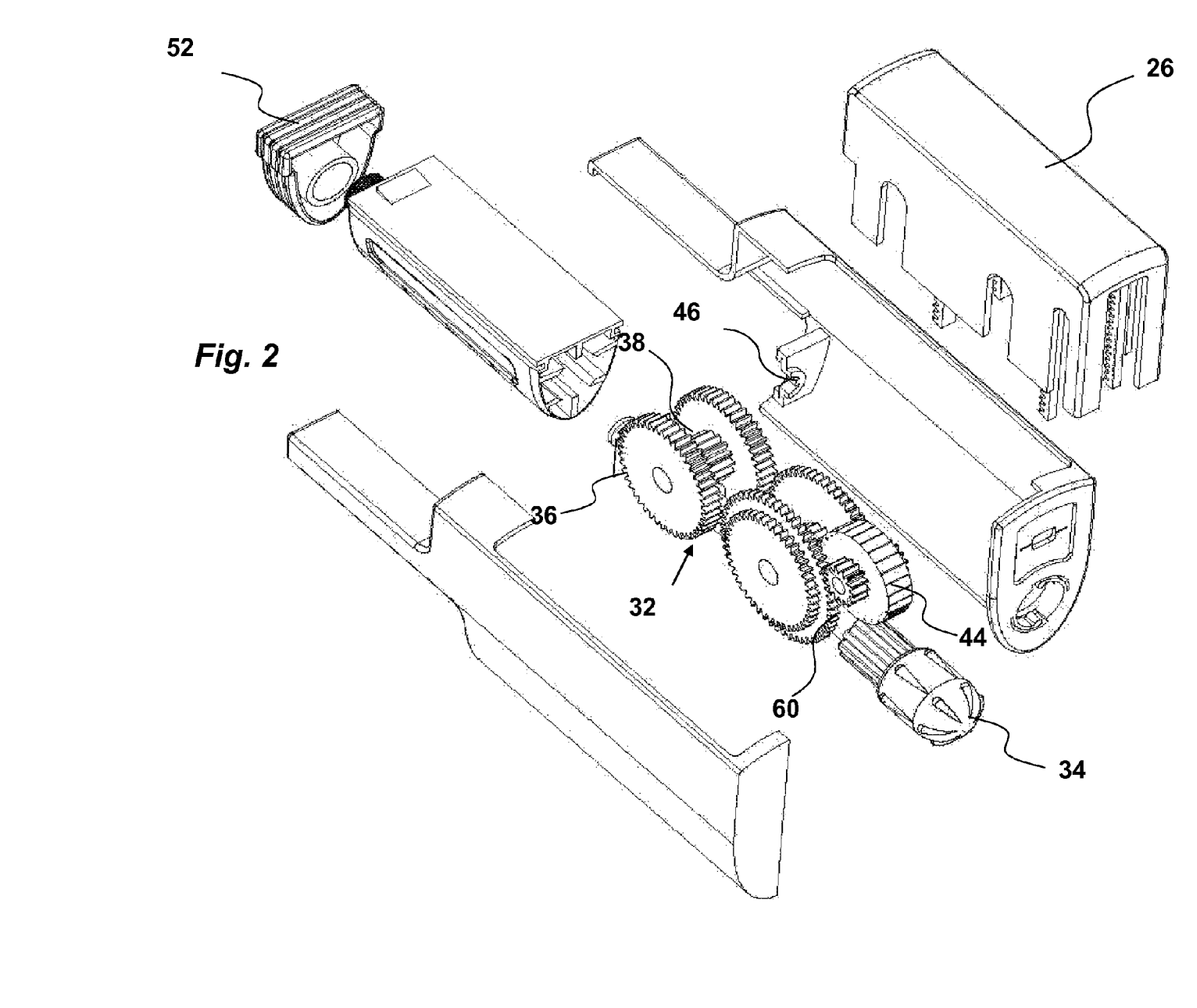
FIG. 2 is an exploded view of the device of FIG. 1.
Figure 3:
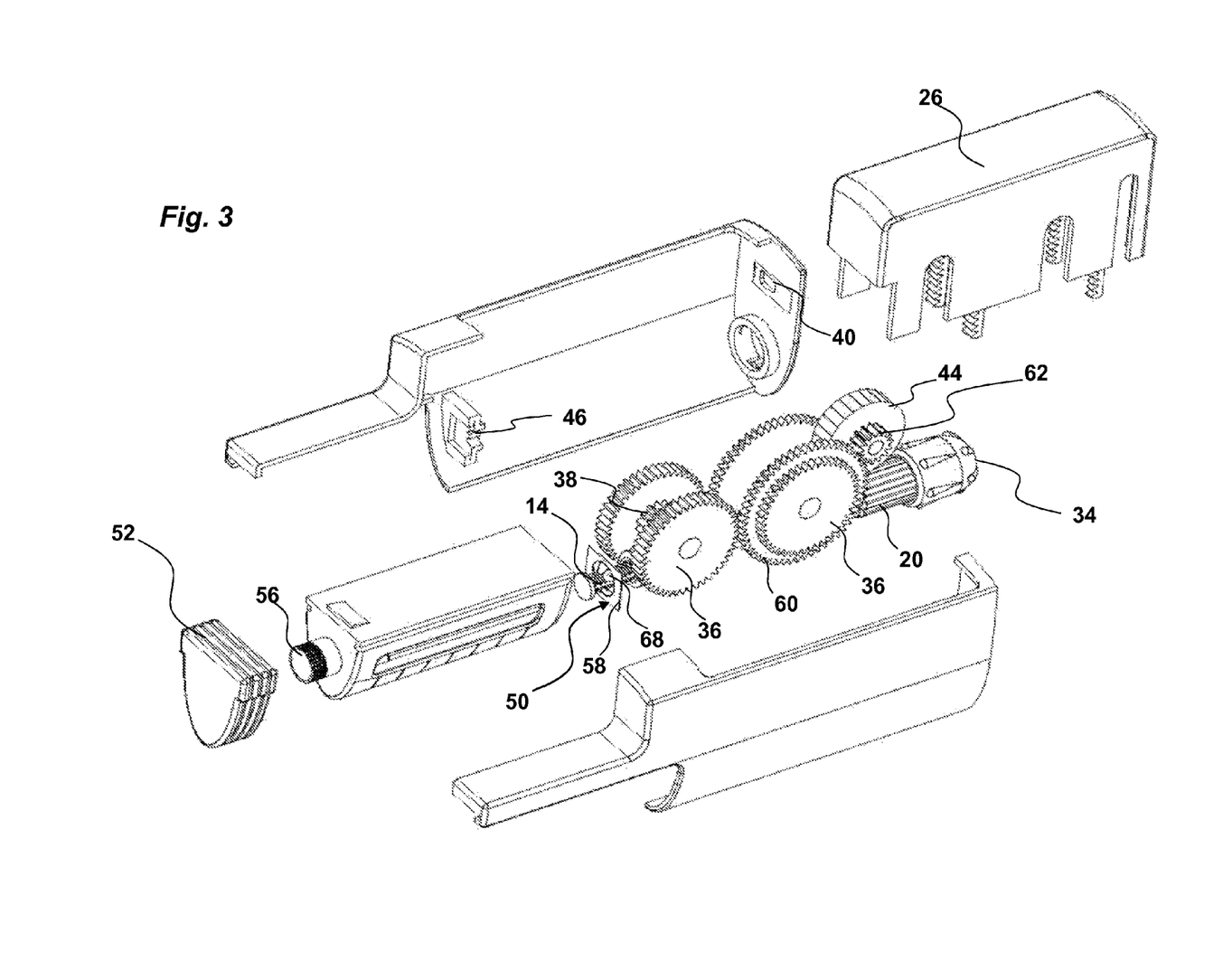
FIG. 3 is an exploded view according to FIG. 2 rotated 90 degrees.
Figure 4A:
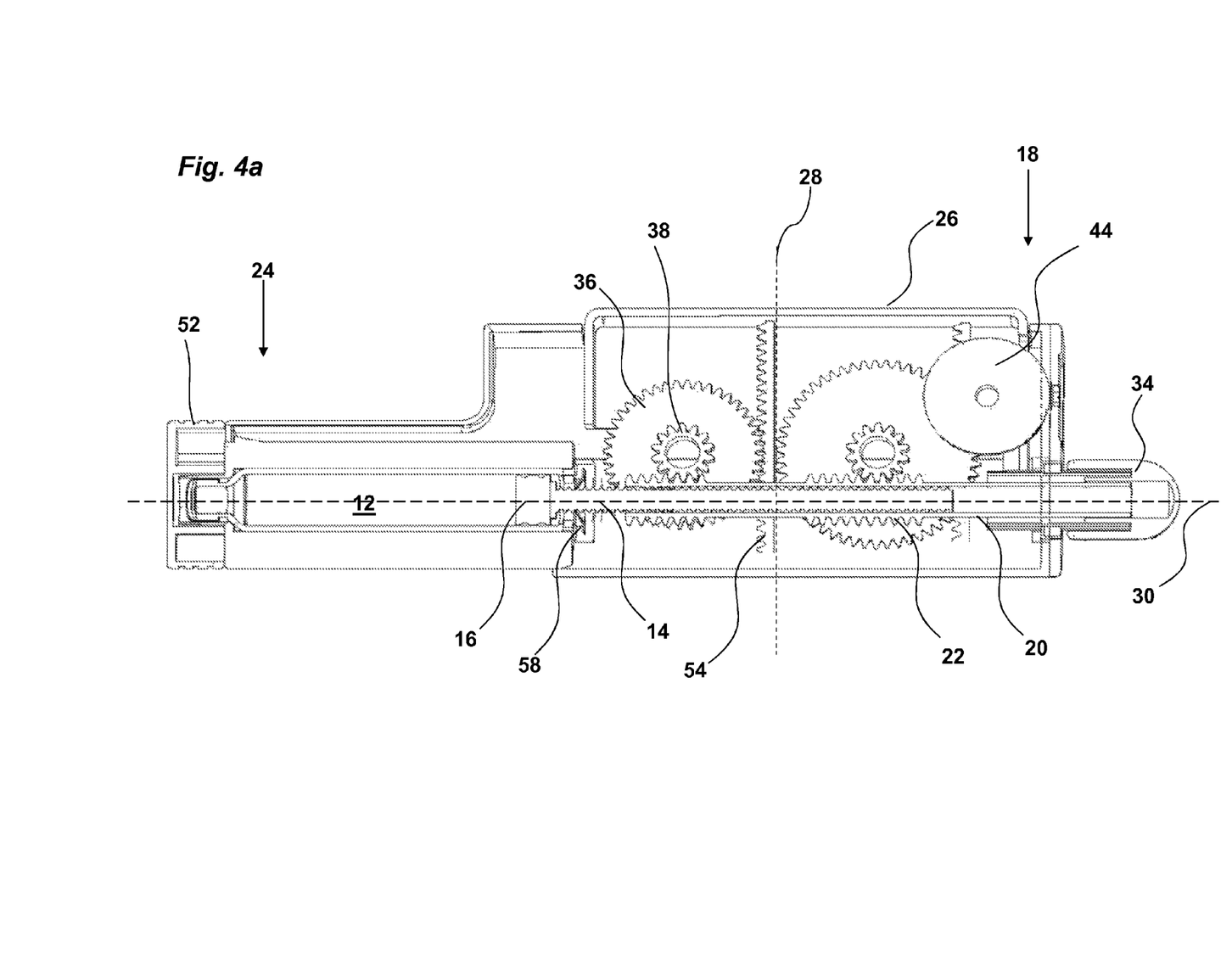
FIGS. 4a-b are cross-sectional views of the device of FIG. 1, FIGS. 5a-c are detailed views of the gear assembly of a medicament delivery device of the present invention.

The device of the exemplary embodiment is intended to function as follows. When a dose of medicament is to be delivered to the user, the protective cap 52 is first removed and a medicament delivery member, e.g. a needle, is attached to said medicament container assembly 12 stored within the housing 10. Before any dosage has been delivered from the injector device, the drive member 14 is retracted as seen in FIG. 4a, and the actuation member 26 is in the initial position. A desired dose is set by means of rotating the dose setting knob 34 which results in the movement of the tubular dose actuation member 20 in the distal direction due to the threaded connection with the drive member 14. Since the drive member 14 is rotationally locked and is only allowed to be longitudinally slidable in the proximal direction said threaded connection between the drive member 14 and the tubular actuation member 20 will lead to movement of the actuation member 20 in a distal direction upon rotation of the dose setting knob 34. The movement of the actuation member 20 will cause the second gear wheels 38 to rotate in a counter clockwise direction with respect to the view seen in FIG. 4a. The rotational movement of second gear wheels 38 is transmitted to said first gear wheels 36 which are arranged in engagement with said gear racks 54 extending in said generally perpendicular direction and being part of the actuation member 26. This results in the gear racks 54 being moved in such a way that also the actuation member 26, which is arranged to be movable in a direction 28 generally perpendicular to a longitudinal axis 30 of the device, is moved out of said housing 10 from the initial position to the dose-set position (not shown). Rotational movement from the second gear wheels 38 is also transmitted to third 60 and fourth 62 gear wheels. Hereby, actuation of the gear assembly 32 is initiated by movement of said dose actuation member 20 and rotation is transmitted via said gear wheels to move the indicia 42 in such a way that a user can interrupt rotation of the dose setting knob 34 when the right dosage is displayed in the dose quantity window 40. Accordingly, at this point the actuation member 26 has been moved to a dose-set position and the injector is ready for delivery.

It is to be understood that it is possible to arrange said indicia 42 on the surface of the actuation member 26 as well as arranging the indicia 42 on the surface of a drum 44 as previously described.

Figure 7:
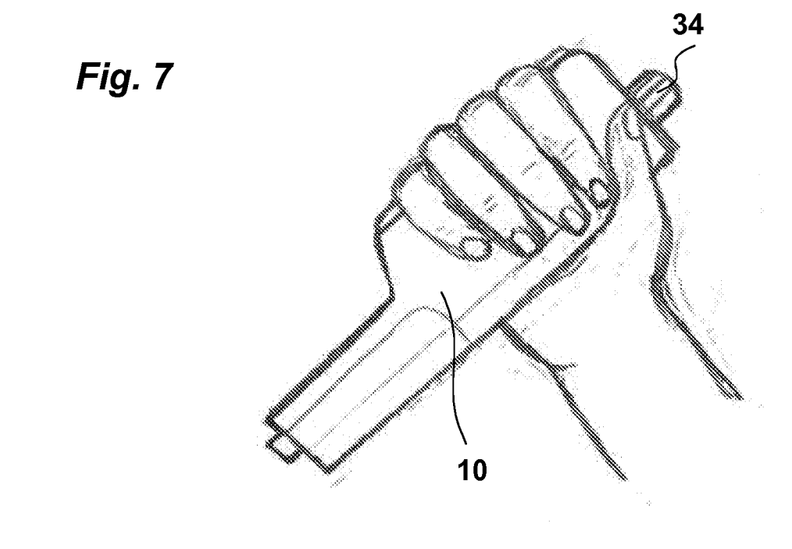
FIG. 7 is a view of a hand of a user gripping a medicament delivery device of the present invention.

Looking at FIG. 7 there is shown the principle of gripping a medicament delivery device according to an exemplary embodiment of the invention. Holding the device as shown in FIG. 7 allows for a steady and ergonomic grip where activation of the actuation member 26 may be performed by using a pressing force from all fingers of one hand thereby permitting use also for persons with reduced dexterity in the hands.

Figure 4B:
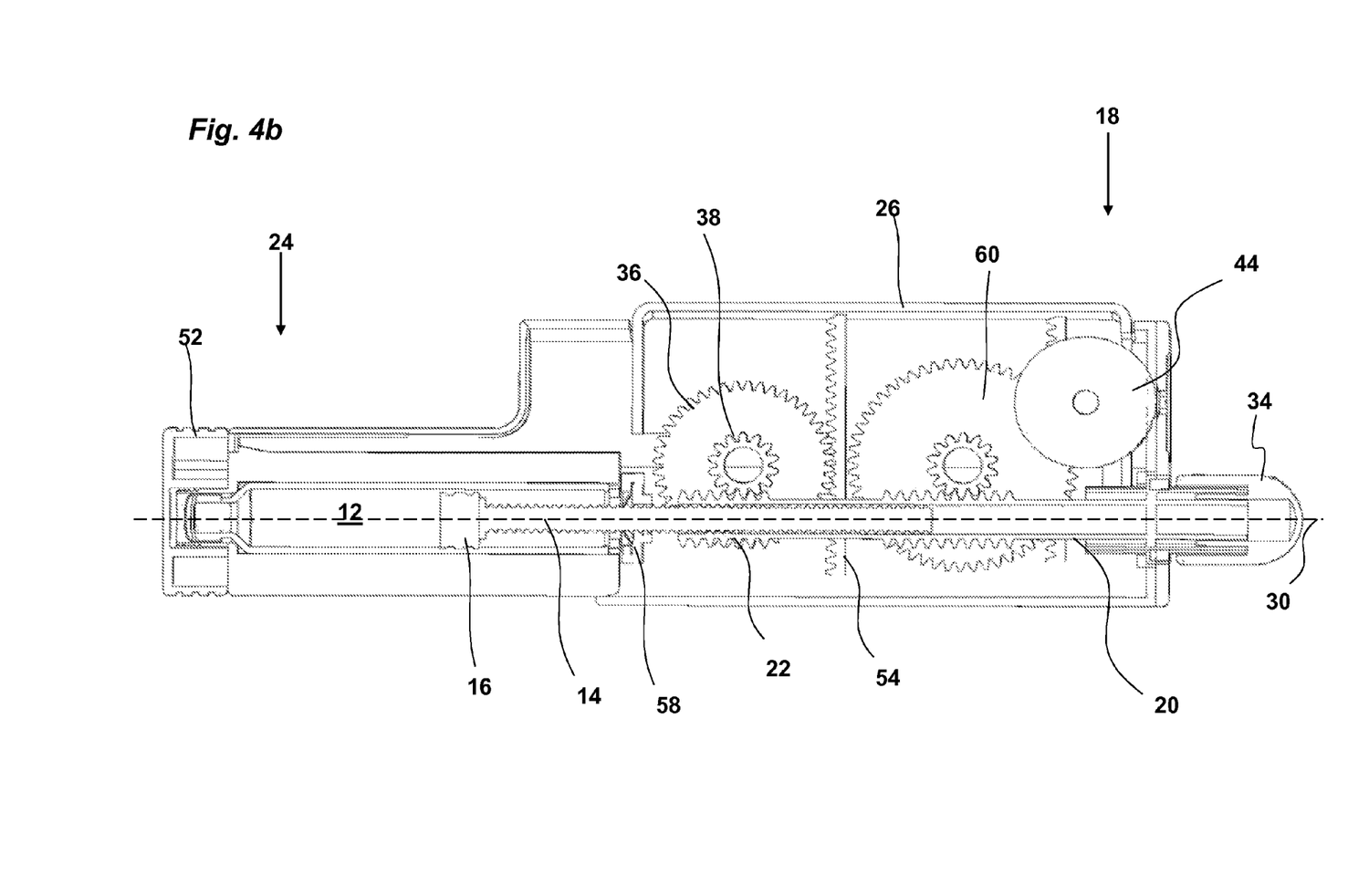

In order to perform an injection the patient grabs the medicament delivery device as shown in FIG. 7 and presses the actuation member 26 inwards against the housing 10. As a result the gear racks 54 will move in a direction generally perpendicular to the longitudinal axis 30 of the device thereby activating the gear assembly 32, meaning generation of a rotation of the first gear wheels 36 thereby also rotation of second gear wheels 38 which, due to the interaction with the gear rack 22, lead to axial movement in a proximal direction of the gear rack 22. Hereby also the drive member 14 will move in a proximal direction because of said threaded connection between the gear rack 22 and the drive member 14. The proximal end of the drive member 14 is acting on a movable stopper 16 (see FIG. 4a-b) inside the container assembly 12, and said movement will result in the stopper 12 pushing against the container assembly 12 thereby expelling the medicament. Once the actuation member 26 has been pressed towards the housing 10 into a fully retracted position, corresponding to the initial state, the predetermined volume of medicament has been completely expelled. At this point the drive member 14 has advanced to a more proximal position compared to before the injection, for instance as seen in FIG. 4b. Said procedure is repeated until the drive member 14 has reached an end position towards the proximal end 24 of the injector device whereupon it is disposed of.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a housing having opposite distal and proximal ends and configured to store a medicament container assembly;
   a drive member interactively connected to said medicament container assembly for expelling a dose of medicament;
   a dose actuation assembly operably connected to said drive member; and
   an actuation member interactively connected to said housing and to said dose actuation assembly by a gear assembly;

wherein the actuation member comprises gear racks extending in a direction generally perpendicular to a longitudinal axis of the device and configured for engagement with the gear assembly, whereby said actuation member is movable in a direction generally perpendicular to the longitudinal axis from an initial position, in which the actuation member is positioned within the housing, to a dose-set position, in which a portion of the actuation member protrudes a distance proportional to a set dose from a longitudinal surface of the housing when the dose actuation assembly is manually operated for setting a dose; and the actuation member is configured to be manually operated in a direction generally perpendicular to the longitudinal axis from the dose-set position to the initial position for driving the dose actuation assembly and thereby the drive member.

2. The medicament delivery device according to claim 1, wherein said gear assembly comprises first gear wheels, and second gear wheels fixedly attached to said first gear wheels; said first and second gear wheels are rotatably connected to the housing; and said first gear wheels have a pitch circle diameter larger than a pitch circle diameter of said second gear wheels for providing a gear ratio.

3. The medicament delivery device according to claim 2, wherein the dose actuation assembly comprises a tubular dose actuation member and a dose setting knob connected to each other.

4. The medicament delivery device according to claim 3, wherein said tubular dose actuation member and said drive member are interactively connected to each other by threads arranged on an outer surface of the drive member and on an inner surface of the tubular dose actuation member.

5. The medicament delivery device according to claim 4, wherein said tubular dose actuation member comprises a gear rack on its outer circumferential surface; and said gear rack is configured to interact with said second gear wheels.

6. The medicament delivery device according to claim 5, wherein the gear racks of the actuation member are configured for engagement with said first gear wheels, such that when said dose setting knob is rotated for setting a dose, the tubular dose actuation member is moved in a distal direction due to the threaded connection with the drive member, and the actuation member is moved out of said housing from the initial position to the dose-set position.

7. The medicament delivery device according to claim 1, wherein the housing comprises a dose quantity window in which indicia are displayed, and indicia correspond to certain dose quantities.

8. The medicament delivery device according to claim 7, wherein said indicia are arranged on a circumferential surface of a drum that is interactively connected to said first gear wheels through third gear wheels and fourth gear wheels.

9. The medicament delivery device according to claim 8, wherein the third gear wheels are fixedly attached to the first gear wheels, and the fourth gear wheels are fixedly attached to the drum.

10. The medicament device of claim 1, wherein the gear assembly comprises first gear wheels that are rotatably connected to the housing, that are longitudinally spaced apart from each other, and that each engage a respective one of the racks of the actuation member.

11. The medicament delivery device of claim 10, wherein the actuation member is configured for activation by a pressing force from all fingers of one hand.

12. The medicament delivery device according to claim 7, wherein said indicia are arranged on a side surface of said actuation member.

13. The medicament delivery device according to claim 7, further comprising guides configured to act on longitudinally extending grooves arranged on an outer surface of said drive member, thereby enabling longitudinal movement but preventing rotation of said drive member.

14. The medicament delivery device according to claim 7, further comprising a one-way lock arranged to interact with the drive member for enabling longitudinal movement of the drive member only in a proximal direction.

15. The medicament delivery device of claim 7, wherein the device is an injector.

16. The medicament delivery device of claim 1, wherein the actuation member is configured for activation by a pressing force from all fingers of one hand.

17. The medicament delivery device according to claim 1, further comprising guides configured to act on longitudinally extending grooves arranged on an outer surface of said drive member, thereby enabling longitudinal movement but preventing rotation of said drive member.

18. The medicament delivery device according to claim 1, further comprising a one-way lock configured to interact with the drive member for enabling longitudinal movement of the drive member only in a proximal direction.

19. The medicament delivery device of claim 1, wherein the device is an injector.

* * * * *